(12) United States Patent
Iizaki

(10) Patent No.: US 8,795,391 B2
(45) Date of Patent: Aug. 5, 2014

(54) COLOURING COMPOSITION

(75) Inventor: Takeshi Iizaki, Tokyo (JP)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/636,296

(22) PCT Filed: Apr. 14, 2011

(86) PCT No.: PCT/EP2011/055926
§ 371 (c)(1),
(2), (4) Date: Sep. 20, 2012

(87) PCT Pub. No.: WO2011/131562
PCT Pub. Date: Oct. 27, 2011

(65) Prior Publication Data
US 2013/0008460 A1    Jan. 10, 2013

(30) Foreign Application Priority Data
Apr. 19, 2010  (EP) .................... 10004132

(51) Int. Cl.
*A61Q 5/10* (2006.01)
*A61K 8/41* (2006.01)
*A61K 8/46* (2006.01)
*A61K 8/92* (2006.01)

(52) U.S. Cl.
CPC . *A61Q 5/10* (2013.01); *A61K 8/416* (2013.01); *A61K 8/463* (2013.01); *A61K 8/92* (2013.01)
USPC ............... 8/405; 8/406; 8/435; 8/455; 8/540; 8/580; 8/606

(58) Field of Classification Search
CPC ......... A61Q 5/10; A61Q 8/416; A61Q 8/463; A61Q 8/92
USPC ............ 8/405, 406, 408, 554, 580, 606, 435, 8/540
See application file for complete search history.

(56) References Cited

U.S. PATENT DOCUMENTS

| | | | |
|---|---|---|---|
| 5,089,257 A | 2/1992 | Schrader et al. | |
| 7,842,100 B2 * | 11/2010 | Matsunaga et al. | 8/405 |
| 2008/0216253 A1 * | 9/2008 | Noecker et al. | 8/407 |

FOREIGN PATENT DOCUMENTS

| | | |
|---|---|---|
| EP | 1 291 006 A1 | 3/2003 |
| EP | 2 151 233 A1 | 2/2010 |
| JP | 2003-238370 A | 8/2003 |
| WO | 2008/070566 A1 | 6/2008 |

OTHER PUBLICATIONS

International Search Report dated Jul. 21, 2011, mailed Aug. 2, 2011.

* cited by examiner

*Primary Examiner* — Eisa Elhilo
(74) *Attorney, Agent, or Firm* — Norris McLaughlin & Marcus PA

(57) ABSTRACT

The present invention relates to an aqueous oxidative coloring composition for keratin fibers especially human hair with improved conditioning effect, improved color fastness against washing and for achieving homogeneous even coloration. The object of the present invention is an aqueous composition for coloring keratin fibers especially human hair, based on at least one oxidative dye precursor, optionally at least one coupling agent and/at least one direct dye and furthermore comprising in a cosmetically acceptable medium at least one anionic surfactant, at least one branched fatty acid and at least one quaternary ammonium surfactant.

15 Claims, No Drawings

COLOURING COMPOSITION

This application is a 371 application of PCT/EP2011/055926 filed Apr. 14, 2011, which claims foreign priority benefit under 35 U.S.C. §119 of European Application No. 10004132.6 filed Apr. 19, 2010.

The present invention relates to an aqueous oxidative colouring composition for keratin fibres especially human hair with improved conditioning effect, improved colour fastness against washing and for achieving homogeneous even colouration.

Oxidative hair colouring has been commonly used for many years. Despite the colours achieved are relatively stable and long lasting, unsatisfactory results have especially been observed with colouring and colour stability on damage hair. Problem is especially big when hair includes parts with various levels of damage. This is especially the case when hair is chemical treated in various ways such as oxidative colouring, bleaching which is at the same time an oxidative treatment in a larger extent and permanent shaping treatments which include reducing and oxidation steps.

One of the problems with fastness of oxidative colours on chemically treated hair is that on one hand colour is relatively stable at the parts where hair is healthy and on the other hand colour is relatively instable on parts which have previously undergone a chemical process.

The present invention starts with the above mentioned problems and aims at providing an oxidative colouring composition for keratin fibres which colours keratin fibres intensive and colours achieved with such composition are especially resistant to washing, and especially importantly colour wash out is uniform from hair at parts with various levels of damage so that hair looks homogeneously coloured for a longer period of time even after consecutive wash cycles.

Present inventor has surprisingly found out that an oxidative colouring composition based on at least one oxidative dye precursor and optionally comprising coupling agents and/or direct dyes which comprises additionally at least one anionic surfactant, at least one branched fatty acid and at least one quaternary ammonium surfactant provides excellent hair colour and colour obtained show high level of wash fastness and appear homogeneous for a long period of time after consecutive wash cycles.

Accordingly the first object of the present invention is an aqueous composition for colouring keratin fibres especially human hair, based on at least one oxidative dye precursor, optionally at least one coupling agent and/or at least one direct dye and furthermore comprising in a cosmetically acceptable medium at least one anionic surfactant, at least one branched fatty acid and at least one quaternary ammonium surfactant.

Further object of the present invention is use of the aqueous composition based on at least one oxidative dye precursor, optionally at least one coupling agent and/or at least one direct dye and furthermore comprising in a cosmetically acceptable medium at least one anionic surfactant, at least one branched fatty acid and at least one quaternary ammonium surfactant for oxidative colouring keratin fibres, especially human hair, an especially for achieving long lasting homogeneous colours.

EP 2151232 and EP 2151232 discloses colouring compositions providing resistant and intensive colours on hair with various level of damage levels based on non-ionic and cat-ionic surfactants. In both documents no mention was made to a composition comprising at least one anionic surfactant.

Composition of the present invention comprises at least one anionic surfactant. In principal any surfactant having anionic character at the pH of the present invention is suitable for the purposes of the present invention. Suitable non-limiting examples are sulphate, sulphonate, carboxylate, aminocarboxylate and alkyl phosphate types. Preferred are carboxylates, sulphates and aminocarboxylate types. More preferred are carboxylates and sulphates and especially preferred are sulphates.

Suitable sulphate surfactants are according to the general structure

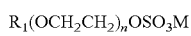

$R_1(OCH_2CH_2)_nOSO_3M$ wherein R is an alkyl chain which may be saturated or unsaturated, straight or branched with 10 to 22 C atoms, preferably 12 to 20 and more preferably 12 to 18 and most preferably 12 to 16 C atoms, n is a number between 0 and 5 and M is a cation and preferably sodium, potassium or ammonium, more preferably sodium or ammonium. Suitable examples are alkyl sulphates such as sodium lauryl sulphate, sodium cetyl sulphate, sodium stearyl sulphate and alkyl ether sulphates such as sodium laureth sulphate, sodium myreth sulphate, sodium ceteth sulphate, sodium oleth sulphate, sodium steareth sulphate, ammonium laureth sulphate, ammonium myreth sulphate, ammonium oleth sulphate, ammonium ceteth sulphate, ammonium steareth sulphate.

Suitable surfactants of the carboxylate type are alkyl polyether carboxylic acids and the salts thereof of the formula

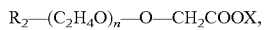

$R_2—(C_2H_4O)_n—O—CH_2COOX$, wherein $R_9$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted.

Suitable anionic aminocarboxylate surfactants are also $C_8$-$C_{22}$-acyl aminocarboxylic acids or the water-soluble salts thereof, such as N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in mixture with the above-named anionic surfactants.

Additional anionic surfactants to mention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Total anionic surfactant concentration varies between 0.1 and 15%, preferably 0.5 and 10%, and more preferably 1 to 7.5% by weight calculated to total composition prior to mixing with oxidizing composition.

All concentrations mentioned within the description refer to the concentration of the respective compound in the composition prior to mixing with any other composition, particularly an oxidizing composition, if necessary, unless otherwise mentioned.

Composition of the present invention comprises at least one branched fatty acid or its respective salt with a chain length of 19 to 24 C atoms. Branched fatty acids are also called iso fatty acids or antesio fatty acids. Suitable ones are 17-methyloctadecanoic acid, 18-methylnonadecanoic acid, 19-methyleicosanoic acid, 16-metyloctodecanoic acid, 17-methylnonadecanoic acid, 20-methylnonadecanoic acid and 18-methyleicosanoic acid. Most preferred is 18-methyl-eicosanoic acid.

Concentration of at least one branched fatty acid is in the range of 0.01 to 10%, preferably 0.02 to 7.5%, more preferably 0.05 to 5% any most preferably 0.1 to 5% by weight calculated to total composition prior to mixing with oxidizing composition.

Compositions of the present invention comprise at least one quaternary ammonium surfactant preferably selected from compounds according to general structures $$R_3\text{-A}\text{—}R_4\text{-B}$$

wherein $R_3$ is a saturated or unsaturated, straight or branched alkyl group with 8 to 24 C atoms, $R_4$ is a straight or branched alkyl group with 1 to 4 C atoms, A is a group selected from O,

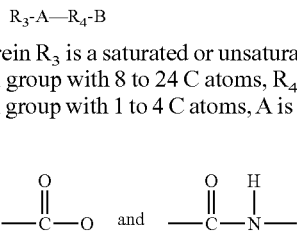

and B is

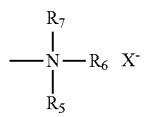

$R_5$, and $R_6$ are the same or different, an alkyl with 1 to 4 C atoms, hydroxyl alkyl with 1 to 4 C atoms and di hydroxyl alkyl with 2 to 4 C atoms, $R_7$ is an alkyl with 1 to 4 C atoms, hydroxyl alkyl with 1 to 4 C atoms or di hydroxyl alkyl with 2 to 4 C atoms and

wherein $R_3$, A and $R_4$ have the above meaning and X is chloride, bromide, methosulfate
and

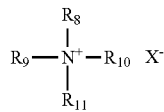

where $R_8$ and $R_9$ are a saturated or unsaturated, branched or straight alkyl chain with 8-24 C atoms, and $R_{10}$ and $R_{11}$ are independent from each other lower alkyl chain with 1 to 4 carbon atoms which may be substituted with one or two hydroxyl group, and X is chloride, bromide or methosulfate.

Preferred quaternary ammonium compounds are according to the above formula wherein A is O.

Non-limiting suitable long-chain quaternary ammonium compounds which are in particular cetyl trimethyl ammonium chloride, dimethyl dicetyl ammonium chloride, trimethyl cetyl ammonium bromide, stearyl trimethyl ammonium chloride, dimethyl stearyl hydroxyethyl ammonium chloride and lauryl trimethyl ammonium chloride. In the preferred embodiment of the present invention, $R_3$ and $R_8$ is saturated or unsaturated, straight or branched alkyl group with 10 to 24 C atoms, more preferably 12 to 22 C atoms and $R_4$ is straight or branched alkyl group with 1 to 4 C atoms, A, B, $R_5$ to $R_{11}$ excluding $R_8$ are same as above. Further non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl methylamine, stearamidopropyl diethylamine, stearamidopropyl dibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenoylpropyl propylamine, behenoylpropyl dihydroxyethylamine, behenoylpropyl hydroxyethylamine, behenoylpropyl dihydroxypropylamine, behenoylpropyl hydroxypropylamine, behenoylpropyl amine, behenoylpropyl methylamine, behenoylpropyl diethylamine, behenoylpropyl dibutylamine, behenoylpropyl butylamine, behenoylpropyl dipropylamine, behenoylpropyl propylamine, behenoylpropyl dihydroxyethylamine, behenoylpropyl hydroxyethylamine, behenoylpropyl dihydroxypropylamine, behenoylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Concentration of at least one alkyl ester/amide alkyl amine or alkyl ester/amide alkyl quaternary amine according to the above general structure is in the range of 0.01 to 20%, preferably 0.02 to 15%, more preferably 0.05 to 10% and most preferably 0.1 to 7.5% by weight, calculated to total composition, prior to mixing with an oxidizing composition.

Composition of the present invention comprises at least one oxidative dye precursor. In principal all oxidative dyes available for hair colouring purposes are suitable within the meaning of the present invention.

As a rule, it is possible to incorporate any developing substances known per se. Special mention is made of p-phenylenediamine, p-aminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxyethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methyl pyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Within the meaning of the present invention above mentioned developers can as well be present as a mixture with each other.

The total concentration of the dye precursors (developing substances) customarily ranges between 0.001 to 10%, preferably 0.01 to 7.5% and more preferably 0.05 to 5%, and most preferably 0.1 to 4% by weight, calculated to the total composition, prior to mixing with an oxidizing composition.

In a further embodiment of the present invention compositions comprise in addition to at least one oxidative dye precursor at least one coupling substance. As a rule any coupling substance customarily used in oxidative hair colouration area is suitable within the meaning of the present invention. Non-limiting coupling substances, are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino)benzene, 1-amino-3-[bis(2'-hydroxy-ethyl) amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. One or more of the above mentioned coupler can also be used in a mixture.

In the hair dyeing compositions according to the invention, the coupling substance(s) as reaction partners of the developing substance(s) are present in approximately the same molecular proportions as the developing substances, i.e. in amounts from 0.001 to 10%, preferably 0.01 to 7.5% and more preferably 0.05 to 5%, and most preferably 0.1 to 4% by weight, calculated to the total composition, prior to mixing with an oxidizing composition.

Further additionally and in a preferred embodiment of the present invention, compositions can comprise at least one direct dye for colouring hair. Suitable direct dyes are cationic, anionic, neutral dyes and mixtures thereof as available commercially from various suppliers and used mainly in semipermanent hair coloration.

One of the suitable direct dyes are cationic dyes. Non-limiting examples are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and their salts such as chloride, methosulfate, bromide etc. and mixtures thereof.

Further suitable direct dyes are anionic dyes. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and their mixtures.

Further suitable dyes for colouring hair within the meaning of the present invention are those of neutral nitro dyes. Suitable non-limiting examples are HC Blue No. 2, HC Blue No.

4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and their mixtures.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitable for use in mixture. In other words, cationic, anionic and nitro dyes are used in mixture within the meaning of the present invention. When using direct dyes of various categories, their compatibility must be taken into account.

Among the direct dyes cationic and nitro dyes are preferred ones. Most preferred ones are cationic direct dyes.

Concentration of direct dyes in the compositions of the present invention is within the range of 0.001 to 10%, preferably 0.01 to 7.5% and more preferably 0.01 to 5%, and most preferably 0.01 to 3% by weight, calculated to total composition, prior to mixing with an oxidizing composition.

In further embodiment of the present invention, compositions comprise mixtures of the hair dyes mentioned above. In other words, a hair dyeing composition comprises at least one direct dye and at least one oxidative dye precursor, optionally at least one coupling substance. Direct dyes are here as well selected from cationic, anionic and nitro dyes. Above mentioned concentration for each class of dyestuff are also valid here.

Colouring compositions according to the present invention can be in the form of emulsion, solution, dispersion, thickened liquid and/or gel. Emulsion form is preferred.

With the term thickened liquid, it is meant that the compositions comprise additionally a thickening agent.

With the term gel it is meant that the compositions comprise additionally a gelling agent and the gelling agent is a polymer forming a shear thinning gel.

The thickening agents include any polymer either natural or synthetic thickening aqueous composition. Examples are cellulose and its derivatives such as hydroxyethylcellulose, guar and its derivatives such as hydroxypropyl guar. In the selection of the thickening agent compatibility with any other components of the formulation should carefully be examined.

The gelling agents include polymers either synthetic or natural forming shear thinning compositions. Examples to the natural polymers are xanthan gum and its derivatives. Synthetic shear thinning polymers may be those of acrylate polymers commercially available for example under trade name Carbopol. In the selection of the geling agent compatibility with any other components of the formulation should carefully be examined.

It should be noted that gelling and thickening agents can also be used in mixture. Concentration of the thickening and/or gelling agents should be in the range of 0.05 to 5%, preferably 0.1 to 2.5% by weight calculated to total content, prior to mixing with an oxidizing composition.

Compositions of the present invention further comprise at least one surfactant selected from non-ionic, cationic, anionic and amphoteric ones and their mixtures. Preferred surfactants are non-ionic, cationic and amphoteric ones and their mixtures. Most preferred are non-ionic and cationic surfactants and their mixtures.

Suitable non-ionic surfactants are alkyl polyglucosides of the general formula

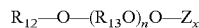

$$R_{12}-O-(R_{13}O)_n O-Z_x$$

wherein $R_{12}$ is an alkyl group with 8 to 18 carbon atoms, $R_{13}$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 50, preferably about 10 and about 30.

Among the non-ionic surfactants mentioned above fatty alcohol ethoxylates are the most preferred ones. Above mentioned non-ionic surfactants can also be used as mixture of one category such as several ethoxylated fatty alcohols or several categories such as mixture of alkyl polyglucoside and ethoxylated fatty alcohol.

As further surfactant suitable for the compositions according to the present invention are amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate.

Total non-ionic surfactant concentration varies between 0.1 and 25%, preferably 0.5 and 20%, and more preferably 1 to 15% by weight calculated to total composition, prior to mixing with an oxidizing composition.

Compositions of the present invention can be in the form of emulsion especially oil in water (O/W) emulsion. Emulsions according to the present invention preferably comprise at least one fatty alcohol with linear of branched alkyl chain. Suitable ones are fatty alcohols having 12 to 22 C atoms in its alkyl chain. Examples are myristyl alcohol, cetyl alcohol, stearyl alcohol, behenyl alcohol and their mixtures. Preferred are cetyl, stearyl and behenyl alcohol and their mixtures i.e. cetearyl alcohol. Fatty alcohols may be included into the compositions of the present invention at a concentration of 0.1 to 25%, preferably 0.5 to 20% and more preferably 1 to 15% by weight calculated to total composition, prior to mixing with an oxidizing composition.

Emulsions should also comprise at least one emulsifier. Suitable emulsifiers are those surfactants mentioned above. Preferred emulsifiers are non-ionic, cationic and anionic surfactant mentioned above. Among the non-ionic surfactant fatty alcohol ethoxylates are the most proffered ones. Among cationic surfactants any cationic surfactant with a single alkyl chain is suitable.

Colouring composition of present invention can comprise additionally fatty acids with 0 to 3 ethylenic bonds and with fatty acyl chain length of 12 to 22 C atom.

Concentration of the fatty acids can be in the range of 0.1 to 10%, preferably 0.1 to 7.5% and most preferably 0.2 to 5% by weight calculated to the total composition, prior to mixing with an oxidizing composition. Fatty acid examples, without limiting the choice, suitable for colouring compositions are myristic acid, palmitic acid, behenic acid, steraic acid, oleic acid, linoleic acid. The most preferred fatty acid is oleic acid.

Compositions of the present invention can comprise additionally hair conditioning compounds such as oils, cationic polymers, non-ionic substances. Oils as conditioners according to the present invention are selected from silicone oils either volatile or non-volatile, natural and synthetic oils. Among silicone oils those can be added to the compositions include either volatile or non-volatile dimethicone, dimethiconol, polydimethylsiloxane, DC fluid ranges from Dow Corning, cyclosiloxanes such as DC 245. Synthetic oils include mineral oil such as paraffin oil and petrolatum.

Arylated silicones have been found to be especially suitable for the compositions of the present invention at a concentration range of 0.01 to 5%, preferably 0.05 to 4% more preferably 0.1 to 3% and most preferably 0.1 to 2.5% by weight calculated to total composition prior to mixing with oxidizing lotion. Non-limiting suitable examples are phenyl methicone, phenyl trimethicone, diphenyl dimethicone, diphenylsiloxy phenyl trimethicone, tetramethyl tetraphenyl trisiloxane, triphenyl trimethicone, tetramethly tetraphenyl trisiloxane and trimethyl pentaphenyl trisiloxane.

Particularly preferred arylated silicone is trimethyl pentaphenyl trisiloxane available from Dow Corning under the trade name DC PH-1555 HRI.

It should be noted that compositions of the present invention can also comprise more than one arylated silicone.

Natural oils suitable are such as olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof.

Lipophilic oily compounds such as fatty acid esters are also suitable for the composition of the present invention. Examples are such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

$R_{14}CO(OCH_2CH_2)_nOH$

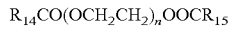

$R_{14}CO(OCH_2CH_2)_nOOCR_{15}$ where $R_{14}$ and $R_{15}$ are independent from each other saturated, unsaturated or branched or non-branched alkyl chain with 7 to 21 C atoms and n is typically 2-100.

Composition of the present invention can comprises cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has especially been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67 and Polyquaternium 87.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

Further cationic polymers are so called aminated silicones such as amodimethicone. The cationic polymers also include the quaternized products of graft polymers from organopolysiloxanes and polyethyl oxazolines described in EP-A 524 612 and EP-A 640 643.

Concentration range for any of the additional conditioners mentioned above is in the range of 0.01 to 10% by weight, preferably 0.05-7.5% by weight, more preferably 0.1-5% by weight calculated to the total composition, prior to mixing with an oxidizing composition.

The compositions according to the present invention can also comprise further agents, such as protein hydrolyzates and polypeptides, e.g. keratin hydrolyzates, collagen hydrolyzates of the type "Nutrilan" or elastin hydrolyzates, as well as, in particular vegetable, optionally cationized protein hydrolyzates, for example "Gluadin".

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition and prior to mixing with an oxidizing composition. Suitable aqueous (e.g. steam-distilled) alcoholic or hydroalcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapone" products and "Herbasol®". Extracts and the preparation thereof are also described in "Hagers Handbuch der pharmazeutischen Praxis", 4th Ed.

The compositions can contain one or more organic solvents such as ethanol. propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvent can be in the range of 1 to 40%, preferably 1 to 25% by weight, calculated to total composition, prior to mixing with an oxidizing composition.

Compositions of the present invention can comprise UV filters for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4.4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher, polysilicone-15. The preferred amount of the UV-absorber ranges from about 0.01% to 2.5%, more preferably from 0.05% to 1% by weight, calculated to the total composition, prior to mixing with an oxidizing composition.

The compositions of the present invention can comprise one or more hair-restructuring agents. The hair restructuring agents preferred are especially the ones disclosed in the German patent DE 197 51 550 C2. Namely they are ceramide type of compounds, fatty acids and phytosterol or their mixtures.

Preferred ceramide compound is cetyl-PG-hydroxyethylpalmitamide.

Preferred fatty acids are those with 10 to 24 carbon atoms and especially with 16 to 24 carbon atoms.

Sterols, especially the phytosterols, are as well preferred hair restructuring agents as disclosed in the above mentioned german patent. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

The concentration of ceramide in the compositions of the present invention can be in the range of 0.01 to 2% and especially 0.01 to 1% by weight calculated to the total weight of the composition. The fatty acids may be contained at a level of 0.01 to 2.5% and especially 0.01 to 1% by weight calculated to the total weight of the composition. Phytosterol concentration of the conditioners is less than 1% and preferably in the range of 0.01 to 0.5% by weight calculated to the total weight of the composition. It should be noted without limiting the use of those ingredients the effect of those hair restructuring ingredients is especially elevated when used in combination with penetration enhancers.

Compositions of the present invention may comprise further at least one compound according to the formula

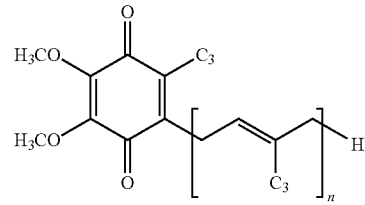

where n is a number from 1 to 10.

The compounds of the above formula are known as Ubiquinone, and also are known as Coenzyme. It should be noted that the compositions of the present invention can certainly comprise more than one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.00001 to 1%, preferably from 0.0001 to 0.75%, more preferably from 0.0001 to 0.5% and most preferably from 0.0002 to 0.5% by weight, calculated to total composition.

Compositions of the present invention may further comprise particulate matter such as synthetic mica. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and are known with their INCI names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.25 to 2.5% by weight calculated to total composition.

The pH of the compositions according to the invention is in the range of 2 to 11 preferably 5 to 11, more preferably 6 to 11, most preferably 6.8 to 11. pH of the compositions can be adjusted by using any organic and/or inorganic acids and alkalizing agents such as ammonium hydroxide and monoethanolamine or their mixtures.

Composition of the present invention can be used after mixing with an oxidizing agent. The oxidizing agents suitable are hydrogen peroxide, urea peroxide, melamin peroxide or perborate salts. The most preferred is hydrogen peroxide, which is used as a lotion containing 2 to 12% by weight, calculated to composition only comprising hydrogen peroxide.

The new composition as a result of mixing colouring and oxidizing composition allows achieving simultaneous lightening and colouring. The mixing ratio of the colouring composition and oxidizing composition should be in the range of 4:1 to 1:4, by weight, preferably 2:1 to 1:3 by weight.

Thus, another object of the present invention is a process for colouring keratin fibres, especially human hair wherein an aqueous composition for colouring keratin fibres especially human hair, based on at least one oxidative dye precursor, optionally at least one coupling agent and/at least one direct dye and furthermore comprising in a cosmetically acceptable medium at least one anionic surfactant, at least one branched fatty acid and at least one quaternary ammonium surfactant is mixed with another composition comprising at least one oxidizing agent and applied onto hair and after processing of 5 to 45 min rinsed off from hair.

Furthermore, compositions of the present invention can comprise all substances customarily found in such preparations. Examples of such substances are complexing agents, preservatives, fragrances, and antioxidants such as sodium sulfit.

Following examples are to illustrate the invention but not to limit.

EXAMPLE 1

|  | % by weight |
| --- | --- |
| Cetearyl alcohol | 11.0 |
| Cocamide MEA | 5.0 |
| Sodium lauryl sulphate | 0.5 |
| Propylene glycol | 2.0 |
| Stearoxypropyl trimonium chloride | 0.7 |
| Oleth-5 | 5.0 |
| 18-Methyl Eicosanoic acid | 0.2 |
| Monoethanolamine | 2.0 |
| Ammonia 25% | 8.0 |
| Ascorbic acid | 0.5 |
| 2,5-Diaminotoluene sulphate | 0.5 |
| Resorcinol | 0.2 |
| 3-Aminophenol | 0.03 |
| 2-Amino-3-hydroxypyridine | 0.03 |
| Sodium sulfite | 1.0 |
| Fragrance, preservative | q.s. |
| Water | to 100 |

For comparative purposes the same composition was also produced without Stearoxypropyl trimonium chloride and 18-Methyl Eicosanoic acid.

The above composition was tested in a half side test against the comparative composition with 10 consumers having shoulder length hair. The above composition was mixed with a composition comprising 6% hydrogen peroxide at a weight ratio of 1 to 1 and applied onto hair and processed for 30 min at a temperature of 40° C. and rinsed off. Comments from the consumers were the side coloured with the inventive composition felt soft and combable and the colour achieved with the inventive composition had significantly more shine, brilliance and vibrancy than the side treated with the comparative composition. Additionally, hair dressers commented that the side coloured with the inventive composition was more homogeneous and even than the side coloured with the comparative composition. 8 volunteers preferred the side according to the invention and 2 could not see any difference.

Additionally, the colour fastness against washing was tested with the above two compositions by placing the coloured hair streaks into a surfactant solution comprising sodium laureth sulphate, an anionic surfactant, at a concentration of 4% by weight, and shaking for 30 min at approximately 30° C. at a speed of 100 rpm and measuring the L, a and b values before and after the test and calculating the ΔE values with the well known equation. Lower ΔE was obtained with inventive composition than that of the comparative composition.

Similar results were obtained with the examples below.

EXAMPLE 2

|  | % by weight |
| --- | --- |
| Cetearyl alcohol | 11.0 |
| Cocamide MEA | 5.0 |
| Sodium lauryl sulphate | 0.5 |
| Propylene glycol | 2.0 |
| Stearoxypropyl trimonium chloride | 0.9 |
| Oleth-5 | 5.0 |
| 18-Methyl octadecanoic acid | 0.9 |
| Monoethanolamine | 2.0 |
| Ammonia 25% | 8.0 |
| Ascorbic acid | 0.5 |
| 2,5-Diaminotoluene sulphate | 0.5 |
| Resorcinol | 0.2 |
| 3-Aminophenol | 0.03 |
| 2-Amino-3-hydroxypyridine | 0.03 |
| Sodium sulfite | 1.0 |
| Fragrance, preservative | q.s. |
| Water | to 100 |

Similar results were observed as in example 1.

EXAMPLE 3

|  | % by weight |
| --- | --- |
| Cetearyl alcohol | 11.0 |
| Cocamide MEA | 5.0 |
| Sodium lauryl sulphate | 0.5 |
| Propylene glycol | 2.0 |
| Polysilicone-9 | 0.1 |
| Stearoxypropyl trimonium chloride | 0.7 |
| Oleth-5 | 5.0 |
| 18-Methyl Eicosanoic acid | 0.2 |
| Monoethanolamine | 2.0 |
| Ammonia 25% | 8.0 |
| Ascorbic acid | 0.5 |
| 2,5-Diaminotoluene sulphate | 0.5 |
| Resorcinol | 0.2 |
| 3-Aminophenol | 0.03 |
| 2-Amino-3-hydroxypyridine | 0.03 |
| Sodium sulfite | 1.0 |
| Fragrance, preservative | q.s. |
| Water | to 100 |

Similar results were observed as in Example 1.

EXAMPLE 4

|  | % by weight |
| --- | --- |
| Cetearyl alcohol | 11.0 |
| Cocamide MEA | 5.0 |
| Sodium steareth sulphate | 0.5 |
| Propylene glycol | 2.0 |
| Stearoxypropyl trimonium chloride | 0.7 |
| Oleth-5 | 5.0 |
| 18-Methyl eicosanoic acid | 0.2 |
| Monoethanolamine | 2.0 |

-continued

| | % by weight |
|---|---|
| Ammonia 25% | 8.0 |
| Ascorbic acid | 0.5 |
| 2,5-Diaminotoluene sulphate | 0.5 |
| Resorcinol | 0.2 |
| 3-Aminophenol | 0.03 |
| 2-Amino-3-hydroxypyridine | 0.03 |
| Sodium sulfite | 1.0 |
| Fragrance, preservative | q.s. |
| Water | to 100 |

Similar results were observed as in the Example 1.

EXAMPLE 5

| | % by weight |
|---|---|
| Cetearyl alcohol | 11.0 |
| Cocamide MEA | 5.0 |
| Sodium ceteth sulphate | 0.5 |
| Propylene glycol | 2.0 |
| Stearoxypropyl trimonium chloride | 0.7 |
| Oleth-5 | 5.0 |
| 18-Methyl octadecanoic acid | 0.2 |
| Monoethanolamine | 2.0 |
| Ammonia 25% | 8.0 |
| Ascorbic acid | 0.5 |
| 2,5-Diaminotoluene sulphate | 0.5 |
| Resorcinol | 0.2 |
| 3-Aminophenol | 0.03 |
| 2-Amino-3-hydroxypyridine | 0.03 |
| Sodium sulfite | 1.0 |
| Fragrance, preservative | q.s. |
| Water | to 100 |

Similar results were observed as in the Example 1.

EXAMPLE 6

| | % by weight |
|---|---|
| Cetearyl alcohol | 11.0 |
| Cocamide MEA | 5.0 |
| Sodium lauryl sulphate | 0.5 |
| Propylene glycol | 2.0 |
| Stearoxypropyl trimonium chloride | 0.7 |
| Ceteareth-5 | 5.0 |
| 18-Methyl octadecanoic acid | 0.2 |
| Monoethanolamine | 2.0 |
| Ammonia 25% | 8.0 |
| Ascorbic acid | 0.5 |
| 2,5-Diaminotoluene sulphate | 0.5 |
| Resorcinol | 0.2 |
| 3-Aminophenol | 0.03 |
| 2-Amino-3-hydroxypyridine | 0.03 |
| Sodium sulfite | 1.0 |
| Fragrance, preservative | q.s. |
| Water | to 100 |

Similar results were observed as in the Example 1.

EXAMPLE 7

| | % by weight |
|---|---|
| Cetearyl alcohol | 11.0 |
| Cocamide MEA | 5.0 |
| Sodium lauryl sulphate | 0.5 |
| Propylene glycol | 2.0 |
| Stearoxypropyl trimonium chloride | 0.7 |
| Ceteareth-5 | 5.0 |
| 18-Methyl octadecanoic acid | 0.2 |
| Monoethanolamine | 2.0 |
| Ammonia 25% | 8.0 |
| Ascorbic acid | 0.5 |
| 2,5-Diaminotoluene sulphate | 0.1 |
| 4,5-diamino-1-hydroxyethyl pyrazol | 0.5 |
| Resorcinol | 0.2 |
| 3-Aminophenol | 0.03 |
| 2-Amino-3-hydroxypyridine | 0.03 |
| Sodium sulfite | 1.0 |
| Fragrance, preservative | q.s. |
| Water | to 100 |

Similar results were observed as in the Example 1.

EXAMPLE 8

| | % by weight |
|---|---|
| Cetearyl alcohol | 11.0 |
| Cocamide MEA | 5.0 |
| Sodium lauryl sulphate | 0.5 |
| Propylene glycol | 2.0 |
| Stearoxypropyl trimonium chloride | 0.7 |
| Ceteareth-5 | 5.0 |
| 18-Methyl octadecanoic acid | 0.2 |
| Monoethanolamine | 2.0 |
| Ammonia 25% | 8.0 |
| Ascorbic acid | 0.5 |
| 4,5-diamino-1-hydroxyethyl pyrazol | 0.5 |
| Resorcinol | 0.2 |
| 3-Aminophenol | 0.03 |
| 2-Amino-3-hydroxypyridine | 0.03 |
| Sodium sulfite | 1.0 |
| Fragrance, preservative | q.s. |
| Water | to 100 |

Similar results were observed as in the Example 1.

The invention claimed is:

1. Aqueous composition for colouring keratin fibres especially human hair, comprising at least one oxidative dye precursor, optionally at least one coupling agent and/or at least one direct dye in a cosmetically acceptable medium, at least one anionic surfactant selected from sulphate, sulphonate, carboxylate and aminocarboxylate surfactants, at least one branched fatty acid and at least one quaternary ammonium surfactant.

2. The composition according to claim 1, wherein the at least one branched fatty acid and its respective salt is selected from those with a chain length 19 to 24 C atoms.

3. The composition according to claim 2, wherein the at least one branched fatty acid is selected from 17-methyloctadecanoic acid, 18-methylnonadecanoic acid, 19-methyleicosanoic acid, 16-methyloctadecanoic acid, 17-methylnonadecanoic acid, 20-methylnonadecanoic acid and 18-methyleicosanoic acid.

4. The composition according to claim 3, wherein the at least one branched fatty acid is 18-methyleicosanoic acid.

5. The composition according to claim 1, wherein the at least one quaternary ammonium surfactant is selected from compounds according to general structure $$R_3\text{-}A\text{-}R_4\text{-}B$$

wherein $R_3$ is a saturated or unsaturated, straight or branched alkyl group with 8 to 24 C atoms, $R_4$ is a straight or branched alkyl group with 1 to 4 C atoms, A is a group selected from O,

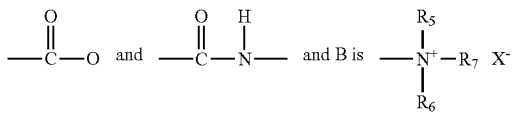

$R_5$, and $R_6$ are the same or different, an alkyl with 1 to 4 C atoms, hydroxyl alkyl with 1 to 4 C atoms and di hydroxyl alkyl with 2 to 4 C atoms, $R_7$ is an alkyl with 1 to 4 C atoms, hydroxyl alkyl with 1 to 4 C atoms or di hydroxyl alkyl with 2 to 4 C atoms and

wherein $R_3$, A and $R_4$ have the above meaning and X is chloride, bromide, methosulfate and

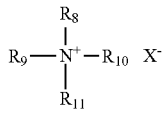

where $R_8$ and $R_9$ are a saturated or unsaturated, branched or straight alkyl chain with 8-24 C atoms, and $R_{10}$ and $R_{11}$ are independent from each other lower alkyl chain with 1 to 4 carbon atoms which may be substituted with one or two hydroxyl group, and X is chloride, bromide or methosulfate.

6. The composition according to claim 5, wherein the at least one quaternary ammonium surfactant is selected from compounds wherein A is O.

7. The composition according to claim 1, comprising at least one fatty alcohol and/or at least one non-ionic surfactant.

8. The composition to according to claim 1, comprising at least one aminated silicone selected from amodimethicone and graft polymers from organopolysiloxanes and polyethyl oxazolines.

9. The composition according to claim 1, comprising at least one cationic direct dye and/or at least one direct nitro dye.

10. The composition according to claim 1, wherein it has a pH between 2 and 11.

11. The composition according to claim 1, further comprising at least one compound selected from thickeners, hair conditioning compound selected from the group consisting of cationic polymers and oils, silicone oils, natural any/or synthetic oils, protein hydrolysates, natural plant extracts, organic solvents, UV filters, ceramides, coenzyme, coated or uncoated synthetic mica, preservatives, fragrances, chelating agents and antioxidants.

12. The composition according to claim 1, comprising at least one oxidizing agent.

13. A process for oxidative colouring hair, wherein a composition according to claims 11 is mixed with a composition comprising at least one oxidizing agent and applied onto hair and rinsed off from hair after processing of 5 to 45 min.

14. The composition according to claim 1 wherein the anionic surfactant is a sulfate.

15. The composition according to claim 14 wherein the anionic surfactant is sodium lauryl sulfate.

* * * * *